(12) United States Patent
Yamamoto et al.

(10) Patent No.: US 9,237,918 B2
(45) Date of Patent: Jan. 19, 2016

(54) ENDOSCOPE TREATMENT TOOL

(71) Applicant: Olympus Corporation, Tokyo (JP)

(72) Inventors: Tetsuya Yamamoto, Hanno (JP); Megumi Kimura, Tokyo (JP); Yasuhiro Tabuchi, Tokyo (JP); Yohei Yoshida, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/219,545

(22) Filed: Mar. 19, 2014

(65) Prior Publication Data
US 2014/0303620 A1    Oct. 9, 2014

Related U.S. Application Data

(63) Continuation of application No. PCT/JP2013/073679, filed on Sep. 3, 2013.

(30) Foreign Application Priority Data

Sep. 10, 2012  (JP) ................................. 2012-198814

(51) Int. Cl.
A61B 18/14     (2006.01)
A61B 18/00     (2006.01)
A61B 17/00     (2006.01)
A61B 17/32     (2006.01)

(52) U.S. Cl.
CPC ........... A61B 18/00 (2013.01); A61B 17/00234 (2013.01); A61B 17/320016 (2013.01); A61B 18/1492 (2013.01); A61B 2018/1405 (2013.01); A61B 2018/1475 (2013.01)

(58) Field of Classification Search
CPC ................. A61B 17/00234; A61B 17/320016; A61B 18/00; A61B 18/1492; A61B 2018/1475; A61B 2018/1405; A61B 2018/1412; A61B 2018/1417; A61B 2018/144; A61B 18/1477; A61B 2017/00269
See application file for complete search history.

(56) References Cited

U.S. PATENT DOCUMENTS

2004/0210215 A1* 10/2004 Okada ............................. 606/45
2010/0081872 A1*  4/2010 Yamamoto et al. ............ 600/104
2012/0220993 A1*  8/2012 Suzuki et al. .................... 606/32

FOREIGN PATENT DOCUMENTS

| JP | A-8-299355    | 11/1996 |
| JP | A-2004-167081 | 6/2004  |
| JP | A-2007-21024  | 2/2007  |
| JP | A-2009-254650 | 11/2009 |
| JP | B2-4455002    | 4/2010  |
| JP | A-2012-120881 | 6/2012  |

OTHER PUBLICATIONS

International Search Report issued in International Application No. PCT/JP2013/073679 mailed Oct. 15, 2013 (with translation).

* cited by examiner

Primary Examiner — Jaymi Della
(74) Attorney, Agent, or Firm — Oliff PLC

(57) ABSTRACT

An endoscope treatment tool includes a sheath having electric insulation; and an electrode unit provided at a distal end portion of the sheath. The electrode unit includes a rod-shaped electrode that is provided to extend in an axis direction of the sheath and is capable of being arranged in a state where the electrode protrudes from the distal end portion of the sheath and is exposed to the outside; and a chip that is fixed in a state where a distal end portion of the electrode is inserted into a concave portion provided in a proximal end surface so as to extend in the axis direction, has a greater external diameter than the external diameter of the electrode, and is formed from a single electric insulation material. The concave portion is formed with a smaller-diameter portion that allows the distal end portion of the electrode to be inserted thereinto.

10 Claims, 9 Drawing Sheets

ENDOSCOPE TREATMENT TOOL

BACKGROUND OF THE INVENTION

1. Field of the Invention

The present invention relates to an endoscope treatment tool used to excise a living body tissue or the like.

This application is a continuation claiming priority on the basis of Japanese Patent Application No. 2012-198814 filed in Japan on Sep. 10, 2012 and based on PCT/JP2013/073679 filed on Sep. 3, 2013. The contents of both the Japanese Patent Application and the PCT Application are incorporated herein by reference.

2. Description of Related Art

The treatment of endoscopically incising living body tissues, such as a mucous membrane, is performed using an endoscope treatment tool including a knife unit (rod-shaped electrode) to which a high-frequency voltage is supplied. As such an endoscope treatment tool, for example, a high-frequency knife disclosed in Japanese Patent No. 4455002 is known.

In this high-frequency knife, a small-diameter rod-shaped first electrode portion is arranged so as to protrude from a distal end of a sheath in an axial direction of the sheath. A distal end portion of the first electrode portion is provided with a second electrode portion radially extending in a direction orthogonal to an axial direction of the first electrode portion. A knife unit is constituted by the first electrode portion and the second electrode portion.

Electrical insulator portions (chips) are provided at distal end portions of the first electrode portion and the second electrode portion.

In the high-frequency knife configured in this way, if the whole knife unit is moved in a transverse direction (a direction orthogonal to an axial direction of the knife unit) while supplying a high-frequency current to the knife unit, a mucous membrane contacting the first electrode portion is incised by the first electrode portion. When it is difficult to move the knife unit in the transverse direction, the whole knife unit is moved in a longitudinal direction (the axial direction of the knife unit). Then, the mucous membrane hooked and lifted by the second electrode portion is incised by the second electrode portion.

In the high-frequency knife disclosed in Japanese Patent No. 4455002, in order to fix the knife unit to the electrical insulator portion, the distal end portion of the knife unit may be attached to the concave portion formed in a proximal end surface of an electrical insulator portion with an adhesive or the like.

A connecting portion between the electrical insulator portion and the knife unit has a high temperature of hundreds of degrees Celcius due to the high-frequency current, and receives reaction forces in various directions when a living body tissue is excised. For this reason, there is a risk that the electrical insulator portion may fall off the knife unit.

In order to solve this problem, a high-frequency treatment tool disclosed in Japanese Unexamined Patent Application, First Publication No. 2007-21024 is suggested.

In the high-frequency treatment tool of Japanese Unexamined Patent Application, First Publication No. 2007-21024, a distal end portion of an electrode unit for treatment that is a knife unit is provided with a retaining portion including a protrusion or a concave portion. After this retaining portion is arranged in an electrical insulating portion forming space constituted by a fixed mold and a movable mold, a melted resin material is filled into an electrical insulating portion forming space. An electrical insulating portion (chip) is formed at the distal end portion of the electrode unit for treatment by cooling and solidifying this resin material.

Additionally, Japanese Unexamined Patent Application, First Publication No. 2007-21024 discloses that a swelling portion having a greater diameter than the external diameter dimension of the electrode unit for treatment is provided at the distal end side portion of the electrode unit for treatment, and the swelling portion is covered with a swelling portion covering insulator cover (chip) constituted by a pair of insulating cover members. By constituting the swelling portion covering insulator cover from the pair of insulating cover member, a shape engaged with the retaining portion of the electrode unit for treatment can be formed in the swelling portion covering insulator cover. Each insulating cover member is joined to the swelling portion by, for example, brazing.

SUMMARY OF THE INVENTION

An endoscope treatment tool related to a first aspect of the present invention includes a sheath which has electric insulation; and an electrode unit which is provided at a distal end portion of the sheath. The electrode unit includes an electrode which has a rod-shaped, is provided to extend in an axis direction of the sheath, and is capable of being arranged in a state where the electrode protrudes from the distal end portion of the sheath and is exposed to an outside; and a chip which is fixed in a state where a distal end portion of the electrode is inserted into a concave portion provided in a proximal end surface of the chip so as to extend in the axis direction, has a greater external diameter than an external diameter of the electrode, and is formed from a single electric insulation material. The concave portion is formed with a smaller-diameter portion that allows the distal end portion of the electrode to be inserted thereinto and has a smaller internal diameter than an internal diameter of the concave portion. A filling member that is capable of being engaged to the smaller-diameter portion is provided further toward a distal end side than the smaller-diameter portion between the concave portion and the electrode.

According to a second aspect of the present invention, in the first aspect, a proximal end of the concave portion may be formed with a larger-diameter portion having a greater internal diameter than the internal diameter of the concave portion, the smaller-diameter portion may be formed further toward a distal end side than the larger-diameter portion in the concave portion, and a collar portion formed at the distal end portion of the electrode may be engaged with the larger-diameter portion.

According to a third aspect of the present invention, in the first aspect, the filling member may include thermosetting resin.

According to a fourth aspect of the present invention, in the first aspect, the filling member may include an elastic member capable of being expandable and contractable in a radial direction of the concave portion.

According to a fifth aspect of the present invention, in the first aspect, the filling member may be configured using a metallic annular member.

According to a sixth aspect of the present invention, in the second aspect, according to the above second aspect, the smaller-diameter portion may be formed so as to be adjacent to the larger-diameter portion.

According to a seventh aspect of the present invention, in the second aspect, according to the above second aspect, an external diameter of the collar portion may be equal to the internal diameter of the larger-diameter portion.

According to an eighth aspect of the present invention, in the first aspect, a concave-convex portion may be formed on an outer peripheral surface of the electrode in a cross-section of a reference plane including an axis of the sheath, and the filling member may be engaged with the concave-convex portion.

According to a ninth aspect of the present invention, in the first aspect, the internal diameter of the smaller-diameter portion may be greater than an external diameter of a distal end portion of the electrode.

DETAILED DESCRIPTION OF THE INVENTION

Hereinafter, an embodiment of an endoscope treatment tool related to the present invention will be described, referring to FIGS. 1 to 20.

Figure 1:
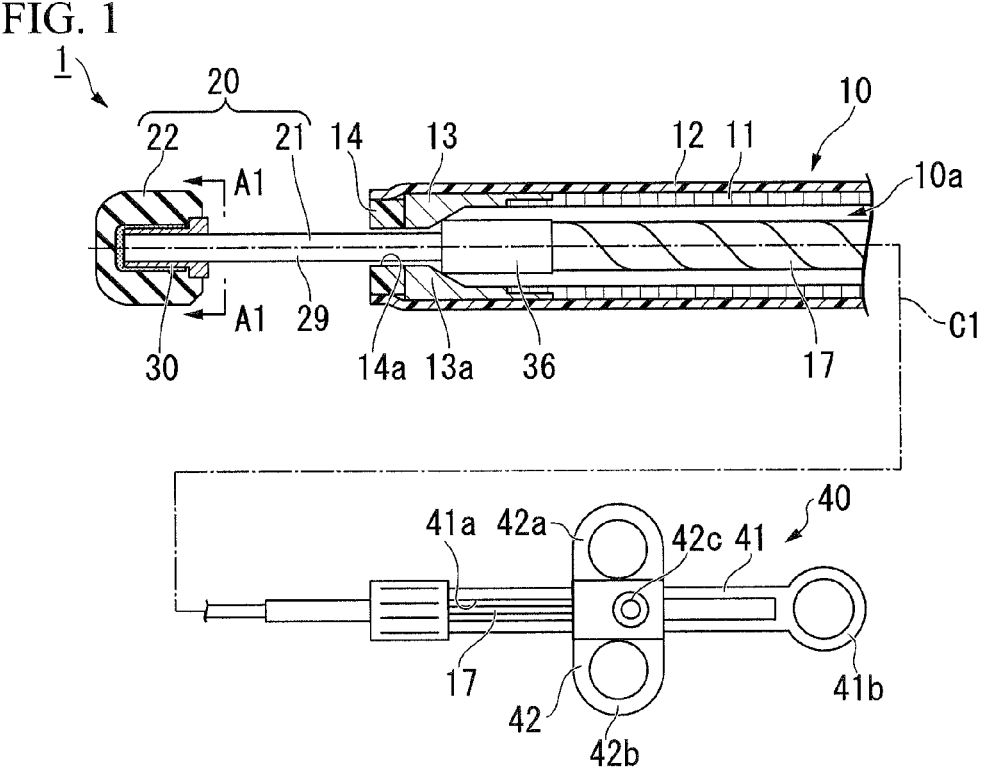
FIG. 1 is a partially broken side view when a high-frequency knife of an embodiment of the present invention is brought into a push state.

As shown in FIG. 1, a high-frequency knife 1 that is the endoscope treatment tool of the present embodiment includes a sheath 10 and an electrode unit 20 provided at a distal end portion of the sheath 10. In addition, in all the following drawings, ratios of the thicknesses or dimensions of respective constituent elements are made appropriately different in order to easily understand the drawings.

The sheath 10 has an external diameter and flexibility such that the sheath is insertable through a channel (not shown) of an endoscope, and has electrical insulation. The sheath 10 has a closely wound coil 11, an insulating tube 12 that covers an outer peripheral surface of the closely wound coil 11, a stopper member 13 that is fixed to an inner peripheral surface of a distal end portion of the insulating tube 12, and an insulating chip 14.

The closely wound coil 11 is configured, for example, by winding a plate-shaped coil with no gap in the direction of an axis C1 of the sheath 10. The closely wound coil 11 has flexibility in that its shape can be easily changed in accordance with changes in shape of an insertion section of the endoscope in a state where the sheath 10 is inserted into the channel of the endoscope.

The insulating tube 12 is formed from, for example, an insulating resin material having heat resistance or flexibility, such as a tetrafluoroethylene material. The external diameter of the insulating tube 12 is formed with an external diameter such that the insulating tube is insertable through the channel of the endoscope.

The stopper member 13 is formed in a tubular shape from a metallic material, such as stainless steel. A distal end portion of the stopper member 13 is formed with a thick portion (having an internal diameter smaller than an internal diameter on a proximal end portion side) 13a that is made thicker on a radial inward side of the sheath 10 than a proximal end portion of the stopper member 13.

An inner peripheral surface and an outer peripheral surface of a coupling portion between the closely wound coil 11 and the stopper member 13 are formed so as to be almost flush with each other.

The aforementioned insulating chip 14 is fixed to the inner peripheral surface of the insulating tube 12 located further toward the distal end side than the thick portion 13a. The insulating chip 14 is fixed to the insulating tube 12 and the stopper member 13. The insulating chip 14 is formed in a substantially columnar shape from a material having insulation, and is formed with a through-hole 14a that passes through the insulating chip 14 in the direction of the axis C1. An inner peripheral surface of the through-hole 14a is formed so as to be substantially flush with an inner peripheral surface of the thick portion 13a.

The operating wire 17 is inserted through a conduit line 10a of the sheath 10 so as to be capable of advancing and retracting in the direction of the axis C1.

Figure 2:
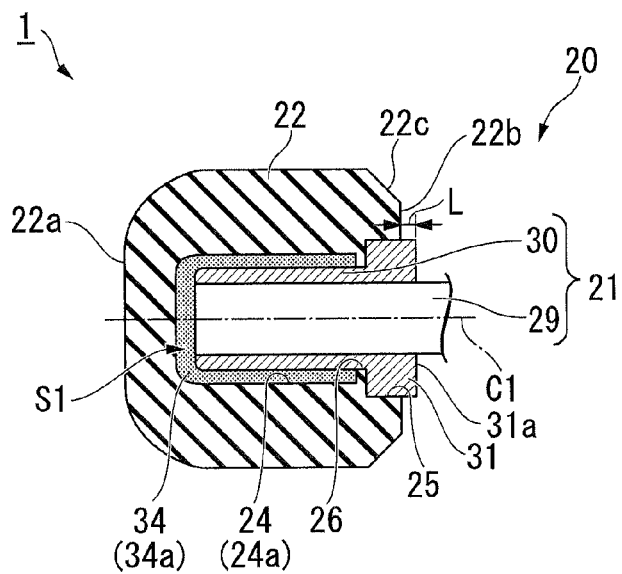
FIG. 2 is a cross-sectional view of a side surface of a distal end portion of the high-frequency knife.

The electrode unit 20, as shown in FIGS. 1 and 2, has a rod-shaped electrode 21 that is provided to extend in the direction of the axis C1, and a chip 22 that is fixed to a distal end portion of the rod-shaped electrode 21.

The chip 22 will first be described below.

Figure 3:
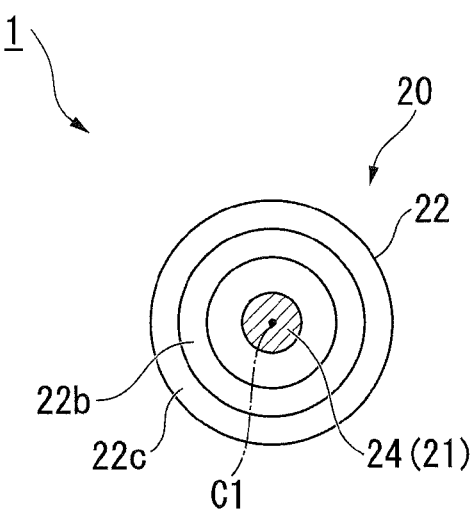
FIG. 3 is a cross-sectional view of cutting line A1-A1 in FIG. 1.

A distal end surface 22a of the chip 22 is formed in the shape of a curved surface that becomes convex toward the distal end side. As shown in FIGS. 2 and 3, a proximal end surface 22b of the chip 22 is flatly formed so as to be orthogonal to the axis C1. The edge of the proximal end surface 22b is formed with a chamfered portion 22c chamfered so as to have an enlarged diameter towards the distal end side.

As shown in FIG. 2, a concave portion 24 is formed in the proximal end surface 22b of the chip 22 so as to extend in the direction of the axis C1. In this example, the concave portion 24 is formed so as to be concave portioned in a columnar shape from the proximal end surface 22b. A proximal end of an inner peripheral surface 24a of the concave portion 24 is formed with a larger-diameter portion 25 having an internal diameter that is greater than the internal diameter of the concave portion 24 and smaller than the external diameter of the chip 22. That is, the larger-diameter portion 25 is open to the proximal end surface 22b of the chip 22.

A smaller-diameter portion 26 having an internal diameter smaller than the internal diameter of the concave portion 24 is formed further toward the distal end side than the larger-diameter portion 25 in the inner peripheral surface 24a of the concave portion 24. The smaller-diameter portion 26 is adjacent to the larger-diameter portion 25. The smaller-diameter portion 26 is formed over the whole circumference of the inner peripheral surface 24a of the concave portion 24. In this example, the cross-sectional shape, taken along a plane (a reference plane Q to be described below) including the axis C1, of the smaller-diameter portion 26 formed so as to protrude to the axis C1 side from the inner peripheral surface 24a is a rectangular shape.

The internal diameter of the smaller-diameter portion 26 is set to a size such that a second electrode 30 (to be described below) of the electrode 21 can be inserted through the smaller-diameter portion.

In the present embodiment, the concave portion 24, the larger-diameter portion 25, and the smaller-diameter portion 26 are formed so as to become rotationally symmetric with respect to the axis C1, respectively.

The chip 22 is formed as a single member from a material having electrical insulation and heat resistance, such as a ceramic material.

The electrode 21 has a first electrode 29 that is formed in an elongated columnar shape, and a second electrode 30 that is formed in a tubular shape and is fitted and fixed to the outside of a distal end portion of the first electrode 29.

The external diameter of the second electrode 30 is set to be slightly smaller than the internal diameter of the smaller-diameter portion 26. A proximal end of the second electrode 30 is formed with a ring-shaped collar portion 31. The external diameter of the collar portion 31 is set to be greater than the external diameter of the second electrode 30 and be equal to or slightly smaller than the internal diameter of the larger-diameter portion 25 of the chip 22. The thickness (the length in the direction of the axis C1) of the collar portion 31 is set to be greater than the length of the larger-diameter portion 25 in the direction of the axis C1. The external diameter of the electrode 21 is set to be smaller than the external diameter of the chip 22.

The first electrode 29 and the second electrode 30 are formed from metal, such as stainless steel. The second electrode 30 is fixed to a distal end of the first electrode 29 by welding or the like.

The electrode 21 and the chip 22 are fixed in a state where the second electrode 30 of the electrode 21 is inserted into the concave portion 24 of the chip 22 and the collar portion 31 of the electrode 21 is engaged with the larger-diameter portion 25 of the chip 22.

Since the external diameter of the collar portion 31 is set to be equal to or slightly smaller than the internal diameter of the larger-diameter portion 25, the electrode 21 inserted into the concave portion 24 of the chip 22 can be prevented from moving in the radial direction or shaking with respect to the chip 22. Additionally, since the thickness of the collar portion 31 is set to be greater than the length of the larger-diameter portion 25 in the direction of the axis C1, the proximal end surface 31a of the collar portion 31 protrudes further toward the proximal end side than the proximal end surface 22b of the chip 22 when a distal end surface of the collar portion 31 is brought into contact with a distal end surface of the larger-diameter portion 25.

By configuring the collar portion 31 in this way, the strength of the collar portion 31 can be ensured by increasing the thickness of the collar portion 31 while suppressing a length L by which the proximal end surface 31a of the collar portion 31 protrudes toward the proximal end side from the proximal end surface 22b of the chip 22 (for example, the length L is about hundreds of micrometers).

A space S1 is formed further toward the distal end side than the smaller-diameter portion 26 between the concave portion 24 of the chip 22 and the electrode 21. The space S1 is formed also between the concave portion 24 and a distal end surface of the electrode 21. The space S1 is filled with a resin member (filling member) 34 made of thermosetting resin with no gap. As the resin member 34, epoxy-based resin or the like can be preferably used. Since the external diameter of the second electrode 30 is set to be slightly smaller than the internal diameter of the smaller-diameter portion 26, the gap between the second electrode 30 and the smaller-diameter portion 26 becomes small. Accordingly, the resin member 34 is prevented from moving (leaking) to the outside from the space S1.

The resin member 34 configured in this way can be locked to the smaller-diameter portion 26 of the chip 22.

As shown in FIG. 1, the first electrode 29 is inserted through the through-hole 14a of the insulating chip 14. A proximal end portion of the first electrode 29 and the distal end portion of the operating wire 17 are mechanically and electrically connected by a stopper receiving portion 36.

The external diameter of the stopper receiving portion 36 is set to be smaller than the internal diameter of the closely wound coil 11 and greater than the internal diameter of the thick portion 13a of the stopper member 13.

In the high-frequency knife 1 of the present embodiment, a proximal end portion of the sheath 10 is provided with an operation unit 40. The operation unit 40 includes an operation unit body 41 that is fixed to the proximal end portion of the sheath 10, and an operating slider 42 that is slidable with respect to the operation unit body 41.

A linear guide shaft portion 41a is formed at the operation unit body 41 between a distal end portion and a proximal end portion of the operation unit body 41. The operation unit body 41 includes a finger-hooking ring 41b at the proximal end portion thereof.

The operating slider 42 is linearly slidable along the guide shaft portion 41a of the operation unit body 41. The operating slider 42 includes finger-hooking rings 42a and 42b in a direction orthogonal to the axis C1, similar to the ring 41b of the operation unit body 41. The operating slider 42 includes the connecting connector portion 42c to which a cord (not shown) that leads to a high-frequency generator (not shown) is electrically connected. A proximal end portion of the operating wire 17 is connected to the operating slider 42.

In the operation unit 40 configured in this way, for example, the operating slider 42 is slidingly operated with respect to the operation unit body 41 by putting the thumb into the ring 41b of the operation unit body 41 and putting the index finger and the middle finger into the rings 42a and 42b of the operating slider 42.

The electrode unit 20 of the high-frequency knife 1 configured in this way is manufactured through the following procedure.

Figure 4:
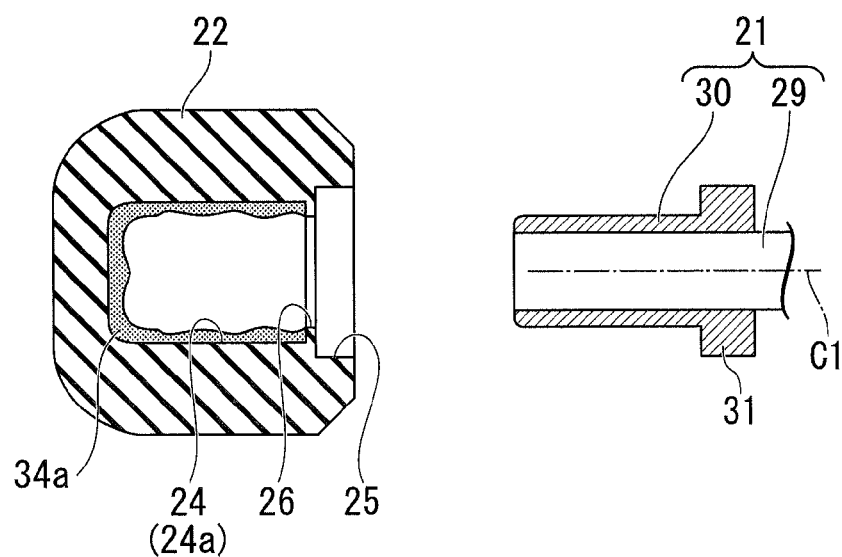
FIG. 4 is a view showing a procedure of manufacturing an electrode unit of the high-frequency knife.

That is, as shown in FIG. 4, the chip 22 is integrally molded as a single member, using a ceramic material, by a mold (not shown). After the chip 22 is molded, an inner mold (core) of the mold arranged in the concave portion 24 is detached from the chip 22. At this time, the inner mold is pulled out to the proximal end side with a certain level or more of force with respect to the chip 22. Accordingly, the internal diameter of the smaller-diameter portion 26 can be increased, and the inner mold can be detached from the chip 22.

The second electrode 30 is fixed to the chip of the first electrode 29 by welding or the like to form the electrode 21.

A fluid resin 34a before the resin member 34 hardens is coated on the inner peripheral surface 24a of the concave portion 24 or the like. As shown in FIG. 2, the second electrode 30 of the electrode 21 is inserted into the concave portion 24 of the chip 22 and the collar portion 31 of the electrode 21 is engaged with the larger-diameter portion 25 of the chip 22.

In this state, if the high-frequency knife 1 is put into, for example, a high-temperature furnace, the fluid resin 34a hardens and forms the resin member 34.

The electrode unit 20 of the high-frequency knife 1 is manufactured by the above process.

In the high-frequency knife 1 configured in this way, as shown in FIG. 1, if the operating wire 17 is pushed into the distal end side with respect to the sheath 10 by moving the operating slider 42 to the distal end side with respect to the operation unit body 41, a push state where the operating wire 17 is pushed into the distal end side is positioned as the stopper receiving portion 36 abuts against the thick portion 13a of the stopper member 13. In this push state, the chip 22 and the second electrode 30 are separated from the distal end side with respect to the insulating chip 14, and the first electrode 29 and the collar portion 31 protrude from the distal end portion of a sheath 10 and are exposed to the outside.

Figure 5:
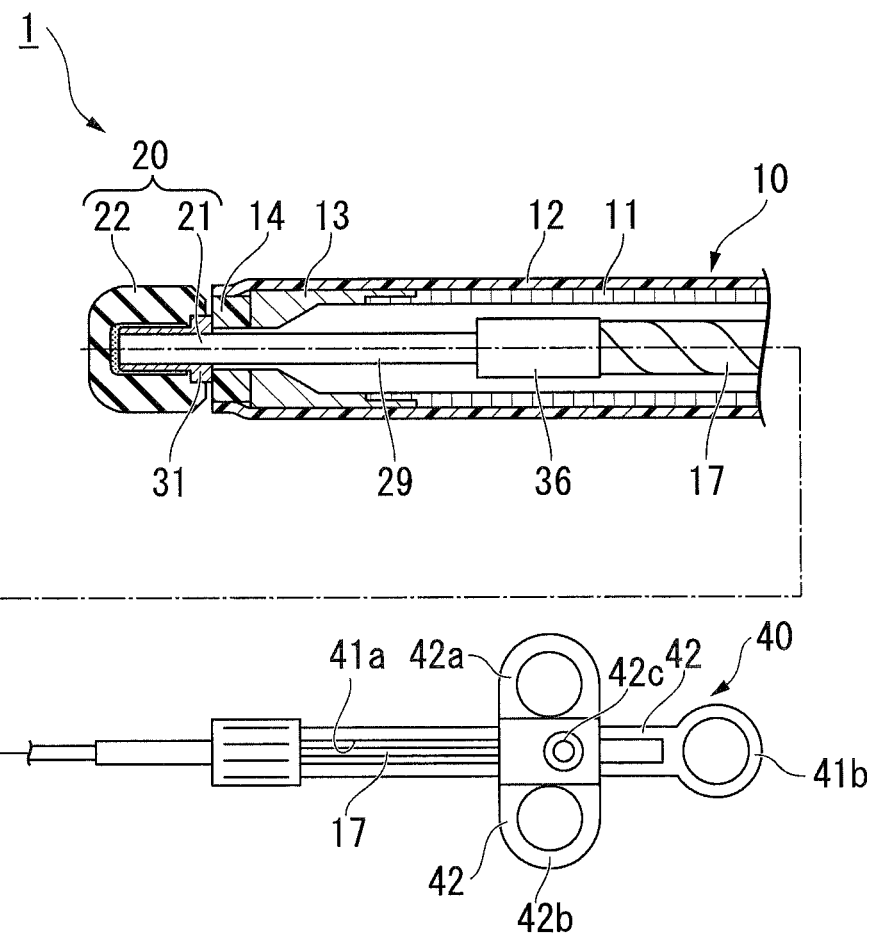
FIG. 5 is a partially cutaway side view when the high-frequency knife is brought into a pull-back state.

On the other hand, if the operating wire 17 is pulled back to the proximal end side with respect to the sheath 10 by moving the operating slider 42 to the proximal end side with respect to the operation unit body 41, as shown in FIG. 5, the collar portion 31 of the electrode 21 abuts against the insulating chip 14, whereby the operating wire 17 pulled back to the proximal end side in the pull-back state is positioned.

In this pull-back state, the first electrode 29 is accommodated within the sheath 10, and the collar portion 31 is hardly exposed to the outside.

Next, the operation of the high-frequency knife 1 configured as mentioned above will be described. In the following, for example, the operation when excision of a mucous membrane within a body cavity is endoscopically performed using the high-frequency knife 1 will be described.

Figure 6:
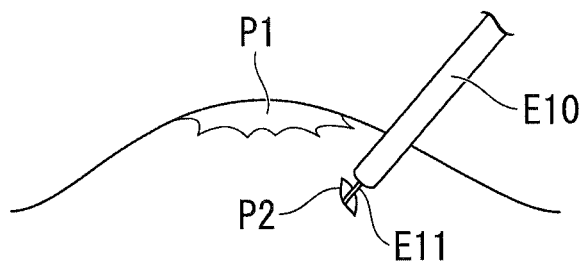
FIG. 6 is a view illustrating a procedure using the high-frequency knife, and is a view showing a state when a hole is made in a portion of a mucous membrane.

First, an injection needle (not shown) is endoscopically introduced into the body cavity through a channel of an endoscope (not shown). Using the injection needle, as shown in FIG. 6, a physiological salt solution is injected into a submucosal layer of a lesioned mucous membrane portion P1 of the body cavity to be excised, and the lesioned mucous membrane portion P1 is caused to bulge.

Next, a counter electrode plate (not shown) is worn by a patient. Thereafter, a high-frequency knife E10 having a well-known needlelike electrode (knife unit) E11 is endoscopically introduced similarly. The initial incision of applying a high-frequency electric current from a high-frequency generator (not shown) to the electrode E11 to make a hole P2 in a portion of the mucous membrane around the lesioned mucous membrane portion P1 is performed. Then, the high-frequency knife E10 is pulled out and removed from the channel of the endoscope.

Figure 7:
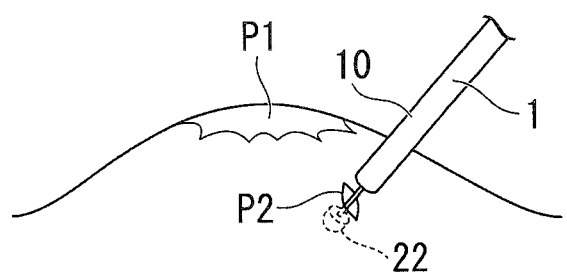
FIG. 7 is a view illustrating the procedure using the high-frequency knife, and is a view showing a state where a chip is inserted into the hole of the mucous membrane.

Subsequently, the high-frequency knife 1 of the present embodiment brought into the pull-back state is introduced into the body cavity via an empty channel of the endoscope. As shown in FIG. 7, the distal end portion of the high-frequency knife 1 is made to protrude from the distal end of the insertion section of the endoscope. Then, the high-frequency knife 1 is brought into the push state, and the chip 22 is separated from the distal end portion of the sheath 10. The chip 22 of the high-frequency knife 1 is inserted into the hole P2 that is initially incised.

Figure 8:
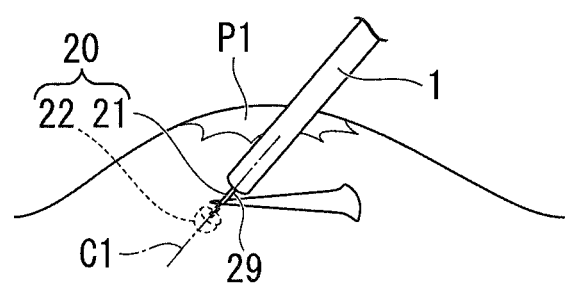
FIG. 8 is a view illustrating the procedure using the high-frequency knife, and is a view showing a state where an electrode is moved in a transverse direction to perform incision.

Thereafter, while a high-frequency current is supplied to the electrode 21, as shown in FIG. 8, the electrode 21 of the high-frequency knife 1 is moved along a predetermined excision direction. At this time, the electrode unit 20 has a high temperature of hundreds of degrees Celcius due to the high-frequency current.

For example, if the electrode 21 is moved in a transverse direction (a direction orthogonal to the axis C1), the mucous membrane contacting the electrode 21 is incised by the electrode 21.

At this time, since the aforementioned length L of the collar portion 31 is suppressed while ensuring strength, the mucous membrane can be reliably incised by the collar portion 31 of the electrode 21.

Figure 9:
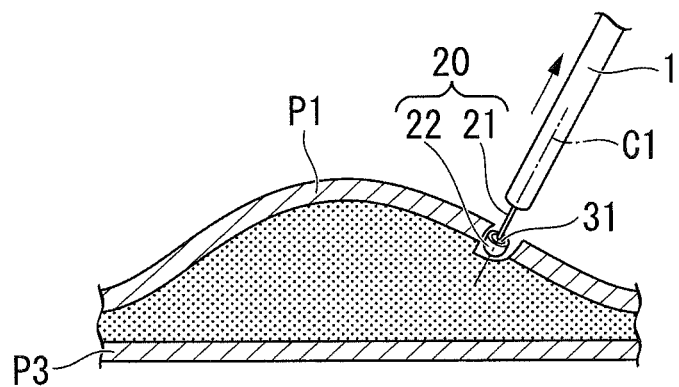
FIG. 9 is a view illustrating the procedure using the high-frequency knife, and is a view showing a state where the electrode is moved in a longitudinal direction to perform incision.
Figure 10:
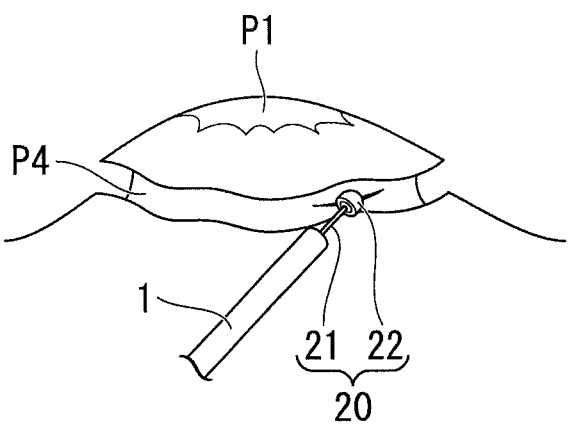
FIG. 10 is a view illustrating the procedure using the high-frequency knife, and is a view showing a state where a lesioned mucous membrane portion is peeled.

When it is difficult to move the electrode 21 in the transverse direction, the mucous membrane hooked and lifted by the collar portion 31 of the electrode unit 20 is incised by coming into contact with the collar portion 31 if the electrode 21 whole is moved in the longitudinal direction (axis C1 direction) as shown in FIG. 9.

The electrode 21 of the high-frequency knife 1 is moved by combining this movement in the longitudinal direction and the aforementioned movement in the transverse direction. Then, the peripheries of the lesioned mucous membrane portions P1 are incised over the circumferential direction of the lesioned mucous membrane portion P1.

For example when the electrode 21 is moved in the longitudinal direction, a force to separate the electrode 21 and the chip 22 from each other may be applied. Even in this case, since the space S1 is provided with the resin member 34, the resin member 34 is locked to the smaller-diameter portion 26 of the chip 22.

A distal end portion of the electrode 21 is covered with the chip 22. Even if the distal end portion of the electrode 21 comes into contact with a non-excised tissue P3 (refer to FIG. 9) by the movement of the electrode 21 in the direction of the axis C1, the high-frequency current supplied to the electrode 21 does not flow to the non-excised tissue P3 by the insulating action of the chip 22.

For this reason, the surgeon does not need to perform the complicated operation of moving the electrode 21 at a constant depth so that the non-excised tissue P3, which is located at a deep portion of the lesioned mucous membrane portion P1 that is a part to be excised, and the electrode 21 do not come into contact with each other.

When the lesioned mucous membrane portion P1 is completely incised over the circumferential direction as mentioned above, as shown in FIG. 10, the electrode 21 is made to abut against an opening P4 obtained by incising the periphery of the lesioned mucous membrane portion P1, the lesioned mucous membrane portion P1 is sequentially incised by the electrode 21 by combining the movement of the high-frequency knife 1 in the transverse direction and the longitudinal direction, and the lesioned mucous membrane portion P1 is peeled.

Then, after the lesioned mucous membrane portion P1 is completely excised and peeled, the high-frequency knife 1 is brought into the push-back state, and is pulled out from the inside of the channel of the endoscope to the hand side. A series of treatments is ended by inserting gripping forceps (not shown) inserted through the empty channel of the endoscope and operating the gripping forceps to take out the lesioned mucous membrane portion P1 endoscopically.

As described above, according to the high-frequency knife 1 of the present embodiment, a high-frequency current is supplied to the electrode 21 via the operating wire 17 in a state where the operating wire 17 is pushed into the distal end side with respect to the sheath 10 to bring the high-frequency knife 1 into the push state and the electrode 21 is exposed. A tissue can be incised by bringing the tissue into contact with the electrode 21.

Since the chip 22 is formed from a single member, it is not necessary to join a plurality of members to constitute a chip unlike the related-art high-frequency treatment tool. Accordingly, the high-frequency knife 1 can be easily manufactured.

The chip 22 is molded by an ordinary mold using a ceramic material or the like without using insert molding. This can keep the manufacturing costs of the high-frequency knife 1 down.

Even if a force to separate the electrode 21 and the chip 22 from each other is applied, the resin member 34 is locked to the smaller-diameter portion 26 of the chip 22. Therefore, the chip 22 can be prevented from falling off the electrode 21.

In the chip 22, the internal diameter of the larger-diameter portion 25 is set to be greater than the internal diameter of the concave portion 24, and the external diameter of the collar portion 31 is set to be equal to or slightly smaller than the internal diameter of the larger-diameter portion 25. Since the movement or shaking of the electrode 21 in the radial direction with respect to the chip 22 is suppressed by the larger-diameter portion 25 having a greater internal diameter than the internal diameter of the concave portion 24, the electrode 21 can be effectively prevented from moving or shaking in the radial direction with respect to the chip 22 when the high-frequency knife 1 is manufactured.

Since the resin member 34 is made of thermosetting resin, the resin member 34 is formed by coating the fluid resin 34a on the concave portion 24 of the chip 22 and hardening the fluid resin 34a in a state where the electrode 21 is inserted into the concave portion 24. After the electrode 21 is inserted into the chip 22, the resin member 34 can be easily formed in the space S1 without injecting a filling member into the space S1.

Since the chip 22 is open on the proximal end side thereof, the chip 22 is deformed more easily on the proximal end side than on the distal end side. Since the smaller-diameter portion 26 of the chip 22 is formed so as to be adjacent to the larger-diameter portion 25 provided at a proximal end of the concave portion 24, the smaller-diameter portion 26 is easily deformed such that the internal diameter thereof is increased. Accordingly, the inner mold of the mold can be easily detached from the molded chip 22.

Since the external diameter of the second electrode 30 is set to be slightly smaller than the internal diameter of the smaller-diameter portion 26, that is, the internal diameter of the smaller-diameter portion 26 is set to be greater than the external diameter of the second electrode 30, the second electrode 30 can be easily inserted into the smaller-diameter portion 26.

The configuration of the high-frequency knife 1 of the present embodiment can be modified in various ways as will be described below.

Figure 11:
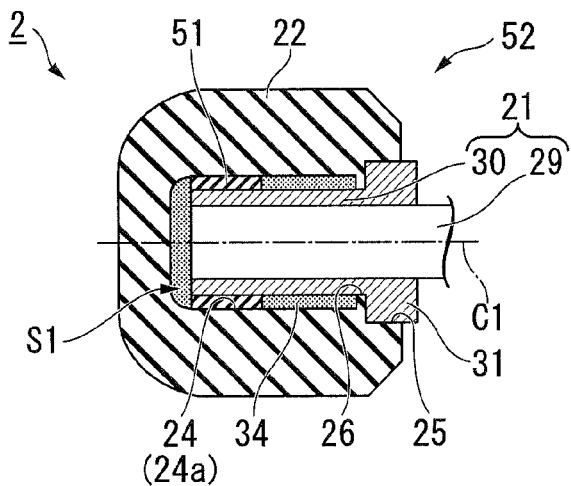
FIG. 11 is a cross-sectional view of a distal end portion of a high-frequency knife of a modified example of the embodiment of the present invention.

As in a high-frequency knife 2 shown in FIG. 11, in the high-frequency knife 1 of the aforementioned embodiment, an elastic member (filling member) 51, such as rubber, may be provided in the space S1 of the chip 22 in addition to the resin member 34. The elastic member 51 is elastically expandable and contractable in the radial direction of the concave portion 24. In this example, the elastic member 51 is arranged so as to be separated to the distal end side with respect to the smaller-diameter portion 26 of the chip 22.

The electrode unit 52 of the high-frequency knife 2 configured in this way is manufactured through the following procedure.

That is, before the electrode 21 is inserted into the concave portion 24 of the chip 22, the elastic member 51 is provided, for example, by sticking the elastic member 51 on the outer peripheral surface of the second electrode 30 of the electrode 21. If the second electrode 30 of the electrode 21 is inserted into the concave portion 24 of the molded chip 22, the elastic member 51 is first reduced in diameter once according to the internal diameter of the smaller-diameter portion 26. However, when the elastic member rides over the smaller-diameter portion 26 to the distal end side, the elastic member is increased in diameter by the elastic force of the elastic member 51 and returns to its original shape.

According to the high-frequency knife 2 of the present modified example configured in this way, the elastic member 51 can be easily arranged in the space S1 of the chip 22 by the elastic force of the elastic member 51 when the high-frequency knife 2 is manufactured.

In the present modified example, since the same effects as the high-frequency knife 1 of the aforementioned embodiment can be exhibited by the elastic member 51 being locked to the smaller-diameter portion 26, the space S1 may not be provided with the resin member 34.

Figure 12:
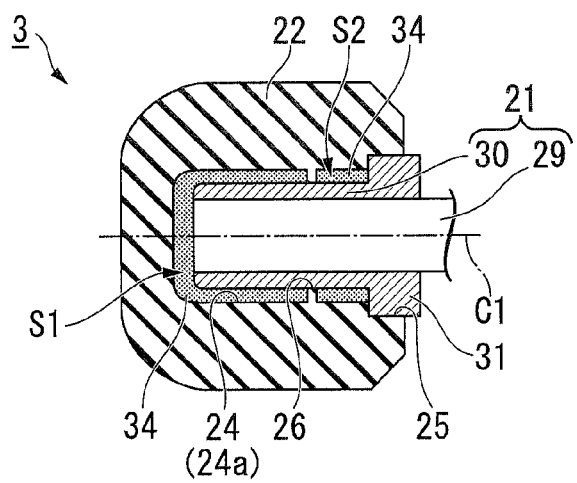
FIG. 12 is a cross-sectional view of a distal end portion of a high-frequency knife of another modified example of the embodiment of the present invention.

As in a high-frequency knife 3 shown in FIG. 12, in the high-frequency knife 1 of the aforementioned embodiment, the smaller-diameter portion 26 may be formed so as to be located further toward the distal end side than the larger-diameter portion 25 and separated from the larger-diameter portion 25. In this modified example, the resin member 34 is provided not only in the space S1 but in a space S2 between the concave portion 24 of the chip 22 and the electrode 21 and between the smaller-diameter portion 26 and the collar portions 31.

The same effects as the high-frequency knife 1 of the aforementioned embodiment can also be exhibited by the high-frequency knife 3 of the present modified example configured in this way.

In the present modified example, the space S2 may not be provided with the resin member 34.

Figure 13:
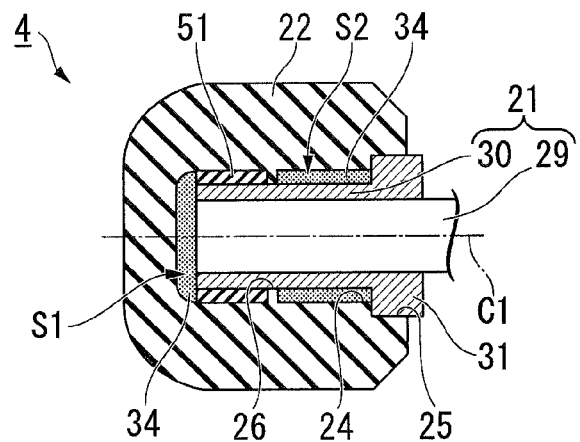
FIG. 13 is a cross-sectional view of a distal end portion of a high-frequency knife of still another modified example of the embodiment of the present invention.

As in a high-frequency knife 4 shown in FIG. 13, in the high-frequency knife 3 of the modified example, the space S1 may be provided with the elastic member 51. In this modified example, the elastic member 51 is arranged so as to come into contact with the smaller-diameter portion 26 closer to the distal end side than the smaller-diameter portion 26.

The same effects as the high-frequency knife 3 of the present modified example can be exhibited also by the high-frequency knife 4 of the present modified example configured in this way.

In the present modified example, the space S1 or the space S2 may not be provided with the resin member 34.

Figure 14:
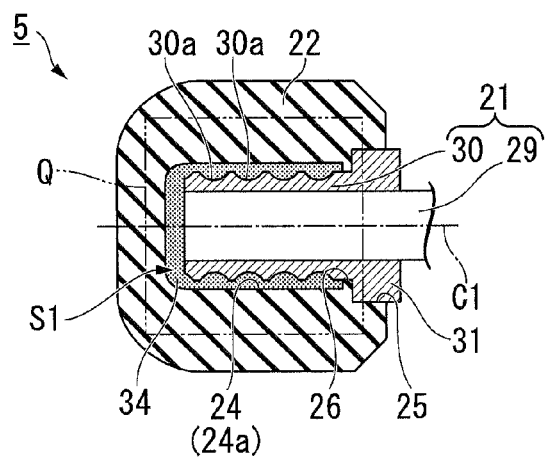
FIG. 14 is a cross-sectional view of a distal end portion of a high-frequency knife of a still further modified example of the embodiment of the present invention.

As in a high-frequency knife 5 shown in FIG. 14, in the high-frequency knife 1 of the aforementioned embodiment, the outer peripheral surface of the second electrode 30 of the electrode 21 may be formed with a concave-convex portion 30a, and the resin member 34 may be engaged with the concave-convex portion 30a in the direction of the axis C1.

Irregularities are formed in a cross-section of the second electrode 30 taken along the reference plane Q including the axis C1 by the concave-convex portion 30a being brought close to or separated from the axis C1 as goes to the proximal end side. The concave-convex portion 30a may be configured by arranging a plurality of annular grooves centered on the axis C1 in the direction of the axis C1, or may be configured by a spiral groove centered on the axis C1.

According to the high-frequency knife 5 of the present modified example configured in this way, the connection strength between the second electrode 30 of the electrode 21 and the resin member 34 is enhanced and the resin member 34 is locked to the smaller-diameter portion 26 of the chip 22. Therefore, the electrode 21 can be more reliably prevented from falling off the resin member 34 in the direction of the axis C1.

In addition, in the present modified example, an concave-convex portion may be further formed on the inner peripheral surface 24a of the concave portion 24, or an concave-convex portion may be formed only on the inner peripheral surface 24a of the concave portion 24.

Figure 15:
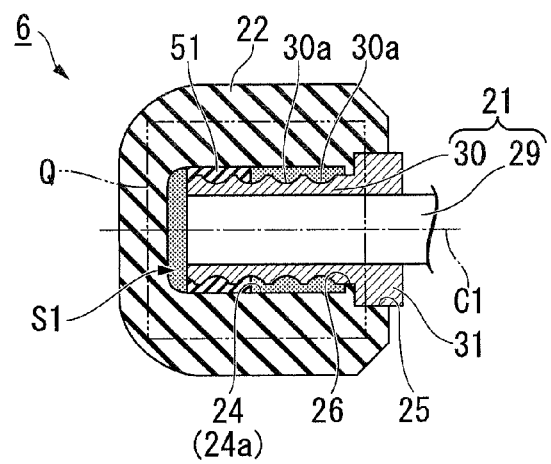
FIG. 15 is a cross-sectional view of a distal end portion of a high-frequency knife of a still further modified example of the embodiment of the present invention.

As in a high-frequency knife 6 shown in FIG. 15, in the high-frequency knife 5 of the aforementioned modified example, the space S1 may be provided with the elastic member 51 engaged with the concave-convex portion 30a. In this modified example, the elastic member 51 is arranged so as to be separated to the distal end side with respect to the smaller-diameter portion 26.

The same effects as the high-frequency knife 5 of the present modified example can also be exhibited by the high-frequency knife 6 of the present modified example configured in this way.

Figure 16:
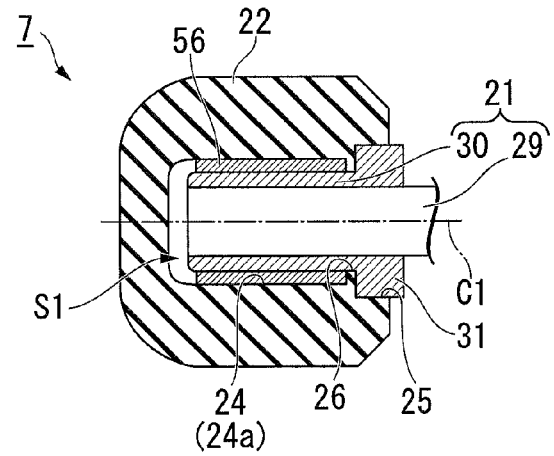
FIG. 16 is a cross-sectional view of a distal end portion of a high-frequency knife of a still further modified example of the embodiment of the present invention.

As in a high-frequency knife 7 shown in FIG. 16, in the high-frequency knife 1 of the aforementioned embodiment, a metallic annular member (filling member) 56 may be provided instead of the resin member 34.

The annular member 56 can be formed, for example, by inserting the electrode 21 into the concave portion 24 of the chip 22, and then, pouring, for example, aluminum or the like with a lower melting point than the chip 22 and the electrode 21, into the space S1 to cool and solidify the poured aluminum.

The same effects as the high-frequency knife 1 of the embodiment can also be exhibited by the high-frequency knife 7 of the present modified example configured in this way.

Although one embodiment of the present invention has been described above in detail with reference to the drawings, specific configuration is not limited to this embodiment, and changes of the configuration are also included without departing from the scope of the present invention. Moreover, the respective configurations shown the respective embodiments and modified examples may be appropriately combined and used.

Figure 17:
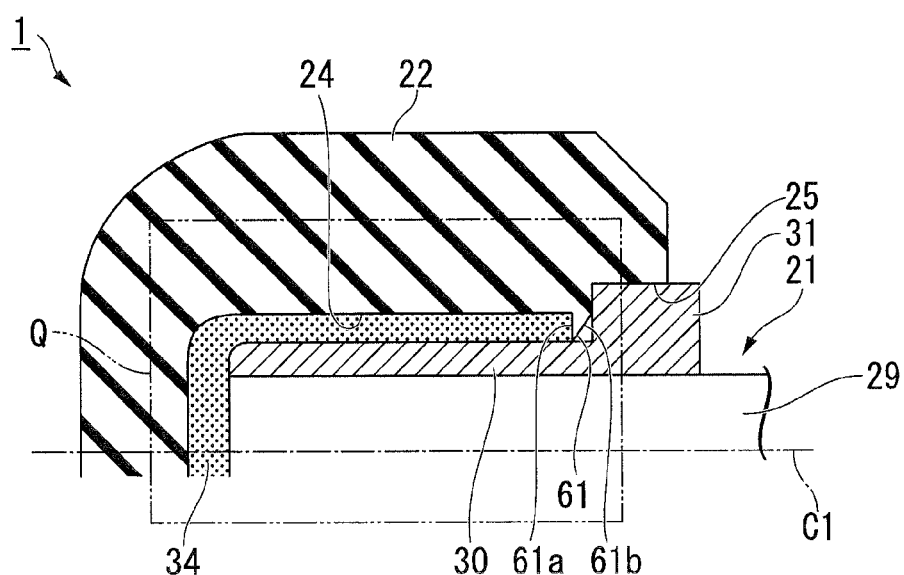
FIG. 17 is a cross-sectional view of a distal end portion of a high-frequency knife of a still further modified example of the embodiment of the present invention.

For example, in the aforementioned embodiment, the cross-sectional shape of the smaller-diameter portion 26 taken along the reference plane Q is a rectangular shape. However, the cross-sectional shape of the smaller-diameter portion taken along this reference plane Q is not limited to this. For example, as shown in FIG. 17, a side 61a on the distal end side is orthogonal to the axis C1. However, a smaller-diameter portion 61 may be formed so that a side 61b on the proximal end side approaches the axis C1 towards the distal end side. The cross-sectional shape of such a smaller-diameter portion 61 may include a triangular shape, a trapezoidal shape, or the like.

By forming the smaller-diameter portion 61 in this way, the resin member 34 can be locked to the side 61a of the smaller-diameter portion 61 to keep the chip 22 from falling off the electrode 21, and the electrode 21 can be guided by the side 61b and the electrode 21 can be easily inserted into the concave portion 24 of the chip 22 when the high-frequency knife 1 is manufactured.

Figure 18:
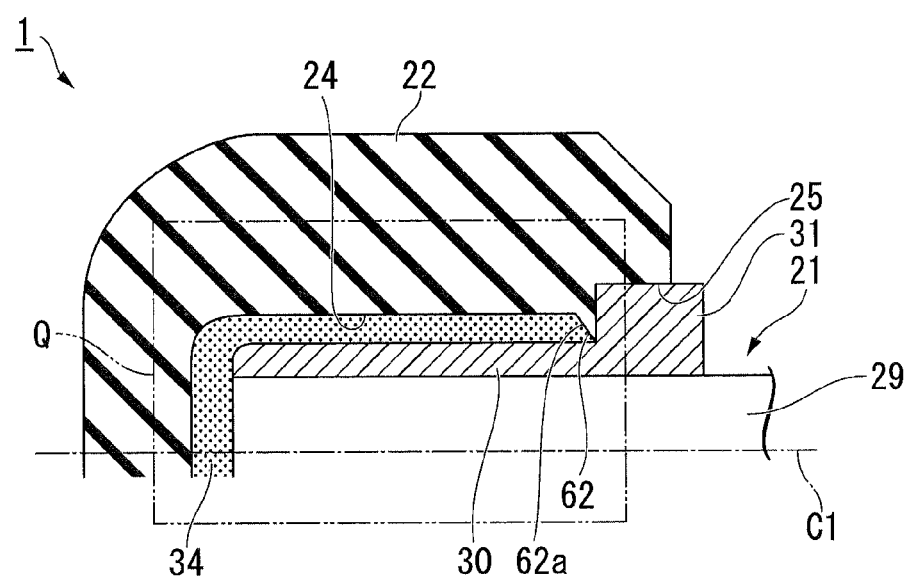
FIG. 18 is a cross-sectional view of a distal end portion of a high-frequency knife of a still further modified example of the embodiment of the present invention.

Additionally, as shown in FIG. 18, a smaller-diameter portion 62 may be formed so as to be separated from the axis C1 as a side 62a on the distal end side goes to the distal end side.

By forming the smaller-diameter portion 62 in this way, the inner mold can be easily detached from the chip 22 when the high-frequency knife 1 is manufactured.

In the aforementioned embodiment and modified examples, the resin member 34 is filled into the space S1 or the space S2 with no gap. However, the resin member 34 may be provided in at least a portion of the space S1 or the space S2. Even if the present invention is configured in this way, the same effects as the aforementioned embodiment and modified examples can be exhibited.

A high-frequency knife may be configured so that the electrode 21 is not accommodated in the sheath 10 but the electrode 21 remains protruding from the distal end portion of the sheath 10.

Since a mucous membrane can be incised by the first electrode 29 of the electrode 21, the electrode 21 of the high-frequency knife 1 may be configured so as not to include the collar portion 31.

Additionally, in the aforementioned embodiment and modified examples, the chip 22 of the high-frequency knife 1 is provided with the larger-diameter portion 25. However, for example when the dimension of the high-frequency knife 1 itself is great, and the collar portion 31 has a thickness such that strength can be ensured, the chip 22 may not be provided with the larger-diameter portion 25.

Figure 19:
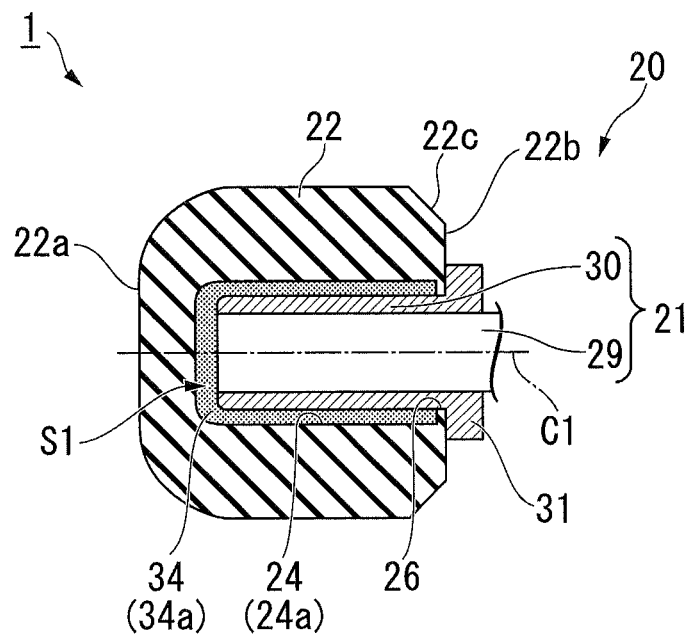
FIG. 19 is a cross-sectional view of a distal end portion of a high-frequency knife of a still further modified example of the embodiment of the present invention.

Specifically, there is provided a configuration in which the whole collar portion 31 engaged with the proximal end surface 22b of the chip 22 as shown in FIG. 19 protrudes further toward the proximal end side than the proximal end surface 22b. When the high-frequency knife 1 is configured in this way, the processing costs of the chip 22 can be further reduced. Moreover, even if a force in the direction of the axis C1 to separate the electrode 21 and the chip 22 from each other acts, the resin member 34 is locked to the smaller-diameter portion 26 of the chip 22. Therefore, the chip 22 can be prevented from falling off the electrode 21.

Figure 20:
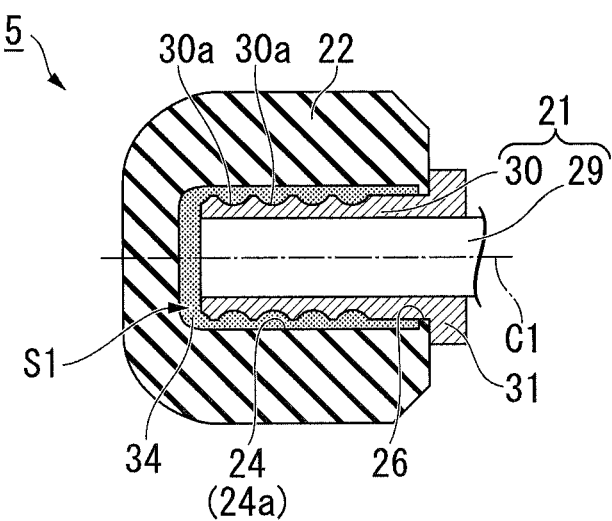
FIG. 20 is a cross-sectional view of a distal end portion of a high-frequency knife of a still further modified example of the embodiment of the present invention.

As another example, there is provided a configuration as shown in FIG. 20 when the larger-diameter portion 25 is not provided in the high-frequency knife 5 of the modified example. Also in this case, the connection strength between the second electrode 30 of the electrode 21 and the resin member 34 can be further enhanced, and the same effects as the high-frequency knife 1 shown in FIG. 19 can be exhibited.

Although the preferred examples of the present invention have been described above, the present invention is not limited to these examples. Additions, omissions, substitutions, and other modifications can be made without departing from the concept of the present invention. The present invention is not to be considered as being limited by the foregoing description, and is limited only by the scope of the appended claims.

What is claimed is:

1. An endoscope treatment tool comprising:

a sheath that has electric insulation; and an electrode unit that is provided at a distal end portion of the sheath, wherein:

the electrode unit includes:

an electrode that has a rod shape is provided to extend in an axial direction of the sheath, and is capable of being arranged in a state where the electrode protrudes from the distal end portion of the sheath and is exposed to an outside of the distal end portion of the sheath; and a chip that is fixed in a state where a distal end portion of the electrode is inserted into a concave portion provided in a proximal end surface of the chip so as to extend in the axial direction, has a greater external diameter than an external diameter of the electrode, and is formed from an electric insulation material, the concave portion has:

a first diameter portion that allows the distal end portion of the electrode to be inserted thereinto, and a second diameter portion having a larger internal diameter than an internal diameter of the first diameter portion, and a filling member that is capable of being engaged to the first diameter portion is provided further toward a distal end side than the first diameter portion between the concave portion and the electrode.

2. The endoscope treatment tool according to claim 1, wherein:

a proximal end of the concave portion has a third diameter portion having a larger internal diameter than the internal diameter of the second diameter portion, and the first diameter portion is formed further toward a distal end side than the third diameter portion in the concave portion, and a collar portion formed at the distal end portion of the electrode is engaged with the third diameter portion.

3. The endoscope treatment tool according to claim 1, wherein the filling member is a resin member.

4. The endoscope treatment tool according to claim 1, wherein the filling member includes an elastic member capable of being expandable and contractable in a radial direction of the concave portion.

5. The endoscope treatment tool according to claim 1, wherein the filling member is configured using a metallic annular member.

6. The endoscope treatment tool according to claim 2, wherein the first diameter portion is formed so as to be adjacent to the third diameter portion.

7. The endoscope treatment tool according to claim 2, wherein an external diameter of the collar portion is equal to the internal diameter of the third diameter portion.

8. The endoscope treatment tool according to claim 1, wherein a concave-convex portion is formed on an outer peripheral surface of the electrode in a cross-section of a reference plane including an axis of the sheath, and the filling member is engaged with the concave-convex portion.

9. The endoscope treatment tool according to claim 1, wherein the internal diameter of the first diameter portion is greater than an external diameter of the distal end portion of the electrode.

10. The endoscope treatment tool according to claim 1, wherein the first diameter portion is formed so as to be separated from an axis of the sheath as a side of the first diameter portion goes to a distal end side of the electrode.

* * * * *